US008114642B2

(12) United States Patent
Takaoka et al.

(10) Patent No.: US 8,114,642 B2
(45) Date of Patent: Feb. 14, 2012

(54) **METHOD FOR PRODUCING VITAMIN K2 FROM CULTURE OF *BACILLUS NATTO***

(75) Inventors: Shinsaku Takaoka, Kyoto (JP); Masaharu Yoshida, Konan (JP)

(73) Assignees: Japan Bio Science Laboratory Co., Ltd., Osaka (JP); Daiwa Kasei K. K., Shiga (JP)

( * ) Notice: Subject to any disclaimer, the term of this patent is extended or adjusted under 35 U.S.C. 154(b) by 302 days.

(21) Appl. No.: 11/823,769

(22) Filed: Jun. 28, 2007

(65) Prior Publication Data

US 2007/0254347 A1    Nov. 1, 2007

Related U.S. Application Data

(63) Continuation-in-part of application No. 11/296,942, filed on Dec. 8, 2005.

(30) Foreign Application Priority Data

Dec. 28, 2004 (JP) ................................ 2004-378455

(51) Int. Cl.
    *C12P 7/66*      (2006.01)
(52) U.S. Cl. .......................................... 435/133; 435/41
(58) Field of Classification Search ........................ None
See application file for complete search history.

(56) References Cited

U.S. PATENT DOCUMENTS

| | | | |
|---|---|---|---|
| 4,207,184 A | 6/1980 | Kaiser et al. | |
| 4,306,080 A | 12/1981 | Haase et al. | |
| 4,849,354 A | 7/1989 | Takayama et al. | |
| 5,750,650 A | 5/1998 | Nakanishi et al. | |
| 6,677,141 B2 | 1/2004 | Sumi | |
| 6,730,504 B2 * | 5/2004 | Takaoka ........................ | 435/183 |
| 2004/0043014 A1 | 3/2004 | Moriyama et al. | |
| 2006/0057688 A1 | 3/2006 | Shimatani et al. | |

FOREIGN PATENT DOCUMENTS

| | | | |
|---|---|---|---|
| JP | 11092414 A | 4/1999 | |
| JP | 2001136959 A | 5/2001 | |
| JP | 2001-352929 A | 12/2001 | |
| JP | 2002360220 A | 12/2002 | |
| JP | 2003292414 A | 10/2003 | |
| JP | 2004143138 A | 5/2004 | |
| JP | 2005130727 A | 5/2005 | |

OTHER PUBLICATIONS

JP 11-092414 A, 1999, Machine Translation, pp. 1-8.*
Pinotti et al., Waste Management, 2001, vol. 21, p. 535-542.*
Sato et al., Journal of Industrial Microbiology & Biotechnology, 2001, vol. 26, p. 115-120.*
Ganjidoust et al., Wat. Sci. Tech. 1997, vol. 35, No. 2-3 p. 291-296.*
Tamura et al., Carbohydrate Polymers, 2004, vol. 56, p. 205-211.*
H. Sumi et al., "A novel Fibrinolytic enzyme (nattokinase) in the vegetable cheese Natto; a typical and popular soybean food in the Japanese diet", *Experientia* 43 (1987), Birkhäuser Verlag. CH-4010 Basel/Swilzerland, pp. 1110-1111.
Keiko Nishimura et al., "Natto diet was apparently effective in a case of incipient central retinal vein occlusion", *Ganka Rinsho Ihou*, 1994; vol. 88, No. 9, pp. 53-57, and partial English translation.
Hiroyuki Sumi et al., "Enhancement of the Fibrinolytic Activity in Plasma by Oral Administration of Nattokinase", *Acta Haematologica* 1990; vol. 84, pp. 139-143.
H. Sumi et al., "A Novel Strong Fibrinolytic Enzyme (Nattokinase) in the Vegetable Cheese 'Natto'", *Fibrinolysis*, International Journal of Fibrinolysis and Thrombolysis, Abstracts of the Ninth International Congress, vol. 2, Supplement 1, p. 67 (1988).
Derwent Abstract 1996-421913 [42] JP08208512 Aug. 18, 1996.
Hashida, Isao, "Development of Polymer Coagulant (1", *Mizu-shori gijutsu*, vol. 38, No. 10, 1997, pp. 499-506, partial English translation (2 pp.).
Okada, Minoru, "Improvement of Polymer Coagulant", *Hyomen*, vol. 28, No. 11, 1990, pp. 846(26)-856(36), partial English translation (4 pp.).

\* cited by examiner

*Primary Examiner* — Kade Ariani
(74) *Attorney, Agent, or Firm* — The Webb Law Firm

(57) ABSTRACT

A method for producing vitamin K2 comprising: culturing *Bacillus natto* in a liquid medium to obtain a *Bacillus natto* culture or culture supernatant thereof, wherein the culture or culture supernatant contains vitamin K2; treating the culture or culture supernatant with at least one coagulant selected from the group consisting of an inorganic coagulant and a cationic polymer coagulant, with the proviso that the coagulant excludes chitosan, so as to obtain a treated coagulant to which vitamin K2 is absorbed or aggregated; separating the treated coagulant from the treated culture or culture supernatant, and obtaining an oily product that contains vitamin K2 from the separated coagulant.

2 Claims, No Drawings

METHOD FOR PRODUCING VITAMIN K2 FROM CULTURE OF *BACILLUS NATTO*

CROSS REFERENCE TO RELATED APPLICATIONS

This application is a continuation-in-part of U.S. patent application Ser. No. 11/296,942 filed Dec. 8, 2005, entitled "Method for Producing Foods from Culture of *Bacillus Natto*", which claimed priority to Japanese Patent Application No. 2004-378455 filed Dec. 28, 2004.

BACKGROUND OF THE INVENTION

1. Field of the Invention

The present invention relates to a method for producing a food product containing a thrombolytic enzyme, nattokinase, but containing little or none of a blood coagulation factor, vitamin K2, in particular, a food product made from a culture of *Bacillus natto*.

The present invention also relates to a method for producing vitamin K2 from a culture of *Bacillus natto*.

2. Description of Related Art

It was discovered by Sumi et al. that the *Bacillus natto* produces the thrombolytic enzyme nattokinase (Experientia Vol. 43, pp. 1110-1111 (1987)). The nutritional value of natto (fermented soybeans) and its value as a health food have been highly evaluated. It is known that nattokinase itself acts as a fibrinolytic enzyme. Nattokinase lyses thrombi when natto is ingested as a food, thus nattokinase has the thrombolytic activity. Nattokinase has extremely good characteristics such as having a long half life and retaining its effectiveness for a long period of time. In addition, it has been reported that nattokinase has a therapeutic effect on incipient central retinal vein occlusion although the effect cannot be clearly seen with urokinase, which also has the thrombolytic activity (Nishimura et al., Japanese Review of Clinical Ophthalmology Vol. 88, No. 9, pp. 53-57 (1994)).

Accordingly, food products containing large amounts of nattokinase, for example, powders and encapsulated products made from *Bacillus natto* culture have been marketed as health foods.

On the other hand, *Bacillus natto* is known to product large amounts of vitamin K2. Vitamin K2 is known as an essential element in the blood coagulation system. Vitamin K2 has other physiological functions, and is said to cause absorption difficulties in newborns and osteoporosis in the elderly when it is deficient, and is said to cause disorders such as hemolytic anemia, splenomegaly, nephropathy, and hepatopathy when it is present in excess. Thus, a *Bacillus natto* culture extract contains not only nattokinase as an effector of thrombolytic system but also vitamin K2 as an effector of blood coagulation system.

The required daily intake of vitamin K's for adults is generally 55 to 65 µg. Large amounts of vitamin K's are contained in foods such as seaweed, broccoli and the like. Vitamin K's are produced by enterobacteria. Also, vitamin K's can be produced by *Bacillus natto* that grow in the intestines with ingesting natto. Therefore, it is said that the required intake of vitamin K2 can be satisfied with a normal diet. Thus, it is generally not necessary to supplement vitamin K2.

Further, problems regarding ingesting natto would occur with patients who receive inhibitors for the vitamin K-dependent blood coagulation factors such as prothrombins VII, IX, and X to prevent thrombosis. If the patients ingest a natto or a *Bacillus natto* culture extract, each of which contains the thrombolytic enzyme nattokinase, for example, in order to prevent thrombosis, they also would intake vitamin K2 at the same time, and the effects of the inhibitors for the vitamin K-dependent blood coagulation factors would be counteracted.

Accordingly, in order to prevent thrombogenesis, it is desirable to obtain a food product made from *Bacillus natto* culture extract in which vitamin K2 has been reduced. Therefore, various methods have been attempted for reducing vitamin K2 in the food product. These methods include extraction of fat soluble vitamin K2 using organic solvents such as hexane. However, there have been some problems in this extraction method as described below. Fat soluble nutrients as well as vitamin K2 would be extracted out and reduced in the food product. The need to remove organic solvents would lead to an increase in the cost of manufacturing. The organic solvents would remain in the food products. The use of organic solvents would cause consumers to resist against ingestion.

A method for removing vitamin K2 using chitosan has been proposed (U.S. Pat. No. 6,730,504). However, chitosan must be dissolved in water before treatment, and is expensive. Therefore, there is a demand for alternative methods for removing vitamin K2.

SUMMARY OF THE INVENTION

The present invention has an object to provide a method for producing a food product from *Bacillus natto* culture from which vitamin K2 has been removed.

The present invention provides a method for producing a food product from *Bacillus natto* culture, said food product containing nattokinase and about 1 µg or less of vitamin K2/g dry weight. The method comprises treating a *Bacillus natto* culture or culture supernatant with at least one coagulant selected from the group consisting of an inorganic coagulant and a cationic polymer coagulant, with the proviso that the coagulant excludes chitosan.

In an embodiment, the inorganic coagulant is at least one inorganic coagulant selected from the group consisting of calcium chloride and poly aluminum chloride.

In a further embodiment, the inorganic coagulant and a phosphorus coagulant are added to the *Bacillus natto* culture or culture supernatant.

In another embodiment, the cationic polymer coagulant is at least one selected from the group consisting of a cationic polysaccharide, a hexamethylenediamine/epichlorohydrin polycondensate and a dimethylamine/epichlorohydrin polycondensate.

In a further embodiment, the cationic polymer coagulant and a polyacrylate are added to the *Bacillus natto* culture or culture supernatant.

In one embodiment, the food product is in the form of one selected from the group consisting of concentrate, paste, powder, granule, capsule, drinkable preparation and tablet.

The present invention further provides a method for producing vitamin K2 comprising: culturing *Bacillus natto* in a liquid medium to obtain a *Bacillus natto* culture or culture supernatant thereof, wherein the culture or culture supernatant contains vitamin K2; treating the culture or culture supernatant with at least one coagulant selected from the group consisting of an inorganic coagulant and a cationic polymer coagulant, with the proviso that the coagulant excludes chitosan, so as to obtain a treated coagulant to which vitamin K2 is absorbed or aggregated; separating the treated coagulant from the treated culture or culture supernatant, and obtaining an oily product that contains vitamin K2 from the separated coagulant.

In an embodiment, the separation is performed by filtration so as to obtain a filtration residue, and vitamin K2 is extracted with an organic solvent from the filtration residue.

The present invention further provides an oily product that contains vitamin K2 obtained by the above mentioned method for producing vitamin K2.

According to the method of the present invention, a food product from *Bacillus natto* culture which contains nattokinase and about 1 μg or less of vitamin K2/g dry weight can be obtained in a simple manner. Since the food product contains only extremely little of vitamin K2, it can prevent excessive intake of vitamin K2 and thrombogenesis in healthy people. Further, the food product is excellent in that people with restriction of vitamin K2 intake can also safely intake nattokinase.

DETAILED DESCRIPTION OF THE INVENTION

A method for producing a food product from *Bacillus natto* culture according to the present invention includes a step of treating a *Bacillus natto* culture (preferably liquid culture) or culture supernatant with a specific agent to substantially remove vitamin K2 in the culture or culture supernatant. Hereinafter, the method of the present invention will be described. Since numerical values of vitamin K2, etc. can vary with any factors such as the type and the culture condition of *Bacillus natto* used, the present invention should not be limited by specific numerical values of vitamin K2, etc. described herein.

Culturing of *Bacillus Natto*

Any microorganisms that are classified as *Bacillus natto* and that can produce nattokinase can be used in the method of the present invention, including *Bacillus natto* which can be isolated from commercially available "natto", fermented soybeans. For example, *Bacillus subtilis* natto can be used. Hereinafter, any microorganisms which can be used in the method of the present invention will be collectively referred to as "*Bacillus natto*".

The culture medium used for *Bacillus natto* should not be limited. The culture medium may be a liquid medium. It is preferable to select a medium by considering that the concentrated medium will be applied as a food product. In the culture medium for *Bacillus natto*, carbon source materials such as starch (for example, corn starch), glucose, and sucros; nitrogen source materials such as defatted soybeans and meat extract; inorganic salts such as calcium carbonate and magnesium chloride can be contained. Fatty acids and the like can be optionally contained in the culture medium. It is preferable that the components of the culture medium are food additive grade.

The method for culturing *Bacillus natto* should not be limited, and incubation with aeration and agitation is preferable for large scale culture. The incubation temperature is not limited as far as *Bacillus natto* can grow. The temperature is preferably about 30 to 45° C., more preferably about 32 to 42° C., and most preferably approximately 37° C. It is preferable that the incubation period be about 3 to 4 days.

Generally, the supernatant after incubation of *Bacillus natto* can include approximately 300 to 600 FU/ml of nattokinase, and approximately 10 to 100 μg of vitamin K2/g dry weight.

Treatment for Removing Vitamin K2

Vitamin K2 can be removed from the culture or culture supernatant using at least one coagulant selected from the group consisting of an inorganic coagulant and a cationic polymer coagulant (excluding chitosan).

Inorganic Coagulant

The inorganic coagulant includes, but is not limited to, calcium chloride, poly aluminum chloride, aluminum sulfate, ferric chloride, polysilicate, and ferrous sulfate. As the inorganic coagulant, calcium chloride, disodium hydrogenphosphate, and poly aluminum chloride can be preferably used. In order to enhance the coagulation by the inorganic coagulant, a combination of the inorganic coagulant with a phosphorus coagulant (e.g., disodium hydrogenphosphate, sodium dihydrogenphosphate, potassium dihydrogenphosphate or tripotassium phosphate) can be used. For example, a combination of calcium chloride and disodium hydrogenphosphate and a combination of poly aluminum chloride and disodium hydrogenphosphate can be preferably used. When using a combination of coagulants, the coagulants may be mixed before their additions, or alternatively, one of the coagulants may be added first, and then the other coagulant may be added. For example, when using a combination of calcium chloride and disodium hydrogenphosphate as a coagulant, disodium hydrogenphosphate can be added first, and then calcium chloride can be added.

Poly aluminum chloride is a compound that is represented by a general formula $[Al_2(OH)_nCl_{6-n}]_m$ and compounds in the range of $1 \leq n \leq 5$ and $m \leq 10$ can be preferably used. Poly aluminum chloride is commercially available, and for example, it is available from TAKI CHEMICAL CO., LTD.

The inorganic coagulant can be added to a culture, which contains microorganisms, or to a culture supernatant, which is obtained by removing microorganisms by means of separation such as centrifugation or filtration. The inorganic coagulant can be added to the culture or the culture supernatant as it is, or in the form of liquid in which the inorganic coagulant is dissolved or dispersed in water. It is preferable to add the inorganic coagulant in the form of liquid. The amount of the inorganic coagulant added can be without limitation and determined depending on the type of the coagulant. The pH in the coagulation reaction can be adjusted as appropriate before or after addition in accordance with the inorganic coagulant used.

As an example, use of a combination of calcium chloride and disodium hydrogenphosphate to treat a *Bacillus natto* culture or culture supernatant will be described below. Disodium hydrogenphosphate is preferably added in an amount of about 1.5 to 7.5 parts by weight, more preferably about 4 to 5 parts by weight per 100 parts by weight of the culture or culture supernatant. Calcium chloride is preferably added in an amount of about 0.5 to 2.5 parts by weight, more preferably about 1 to 1.8 parts by weight per 100 parts by weight of the culture or culture supernatant. For example, disodium hydrogenphosphate is added and dissolved first, and then calcium chloride is added. Thereafter, the pH of the culture or culture supernatant is adjusted preferably in the range of about 7 to 7.4

When treating a *Bacillus natto* culture or culture supernatant with poly aluminum chloride, poly aluminum chloride is added preferably in an amount of about 0.001 to 0.6 parts by weight (about 10 to 6,000 ppm per the solution), more preferably about 0.3 to 0.5 parts by weight (about 3,000 to 5,000 ppm per the solution) per 100 parts by weight of the culture or culture supernatant. The pH of the culture or culture supernatant to which poly aluminum chloride has been added is preferably adjusted in the range of about 4.5 to 5.0.

Cationic Polymer Coagulant

The cationic polymer coagulant includes, but is not limited to, cationic polysaccharides, hexamethylenediamine/epichlorohydrin polycondensates, dimethylamine/epichlorohydrin polycondensates, water-soluble aniline resin hydrochloride, polyethyleneimine, polyamine, polydianildimethylammonium chloride, and hexamethylenediamine. However, the cationic polymer coagulant does not include chitosan. In particular, cationic polysaccharides, hexamethylenediamine/epichlorohydrin polycondensates, and dimethylamine/epichlorohydrin polycondensates can be preferably used. A polyacrylate can be added to the cationic polymer coagulant to enhance the coagulation. For example, a combination of cationic polysaccharides and polyacrylates is preferably used. A cationic polymer coagulant and a polyacrylate may be mixed before additions thereof, or alternatively either one of them may be added first and then the other may be added.

An example of cationic polysaccharides is Kiprogum NGK (trade name: manufactured by NIPPON STARCH CHEMICAL CO., LTD.).

The cationic polymer coagulant can be added to a culture or culture supernatant as it is, or in the form of liquid in which the cationic polymer coagulant is dissolved or dispersed in water. The amount of the cationic polymer coagulant added can be without limitation and determined depending on the type of the cationic polymer coagulant. The pH in the coagulation reaction can be adjusted as appropriate before or after the addition in accordance with the cationic polymer coagulant used.

As an example, use of cationic polysaccharides, hexamethylenediamine/epichlorohydrin polycondensates, or dimethylamine/epichlorohydrin polycondensates to treat a *Bacillus natto* culture or culture supernatant will be described below.

Cationic polysaccharides are preferably added in an amount of about 0.005 to 0.2 parts by weight, more preferably about 0.02 to 0.04 parts by weight per 100 parts by weight of the culture or culture supernatant. The pH of the culture or culture supernatant is preferably adjusted before addition of cationic polysaccharides. The pH is preferably in the range of about 4 to 5, more preferably about 4.5.

The cationic polysaccharides are preferably combined with sodium polyacrylate. They can be used for the treatment in a combination of amounts within the ranges described herein.

The polyacrylate includes, but is not limited to, sodium polyacrylate, potassium polyacrylate, ammonium polyacrylate, lithium polyacrylate, and amine salts of polyacrylate.

Sodium polyacrylate is preferably added in an amount of about 0.005 to 0.2 parts by weight, more preferably about 0.02 to 0.04 parts by weight per 100 parts by weight of the culture or culture supernatant. The pH of the culture or culture supernatant is preferably adjusted before addition of sodium polyacrylate. The pH is preferably in the range of about 4 to 5, more preferably about 4.5.

A hexamethylenediamine/epichlorohydrin polycondensate is preferably added in an amount of about 0.0001 to 0.02 parts by weight (about 1 to 200 ppm per the solution), more preferably about 0.005 to 0.01 parts by weight (about 50 to 100 ppm per the solution) per 100 parts by weight of the culture or culture supernatant. The pH of the culture or culture supernatant to which hexamethylenediamine/epichlorohydrin polycondensate has been added is adjusted preferably in the range of about 6.5 to 7.5, more preferably about 7.

A dimethylamine/epichlorohydrin polycondensate is preferably added in an amount of about 0.0001 to 0.02 parts by weight (about 1 to 200 ppm per the solution), more preferably about 0.005 to 0.01 parts by weight (about 50 to 100 ppm per the solution) per 100 parts by weight of the culture or culture supernatant. The pH of the culture or culture supernatant to which dimethylamine/epichlorohydrin polycondensate has been added is preferably adjusted in the range of about 6.5 to 7.5, more preferably about 7.

Removal of Coagulant

The coagulant is added to the *Bacillus natto* culture or culture supernatant, and the mixture is stirred extensively and then filtrated, for example, using a pressure filtering apparatus, with a filter aid such as pearlite and diatomite to obtain a clear filtrate. Alternatively, the coagulant is added to the culture or culture supernatant, and then a filter aid such as pearlite and diatomite is added thereto, and then the mixture is stirred for an appropriate time and then filtrated, for example, using a pressure filtering apparatus, to obtain a clear filtrate. The filtrate thus obtained may be further treated while, if necessary, adjusting the pH. By treating the *Bacillus natto* culture or culture supernatant with the coagulant, at least about 95%, preferably at least about 99%, and more preferably at least about 99.9%, of the vitamin K2 can be removed, while nattokinase is not almost removed and remains in the filtrate.

Although the coagulant is dissolved or dispersed in the culture or culture supernatant, it is removed by the filter aid, and is not almost contaminated in the filtrate. It is believe that because the coagulant is adsorbed to microorganisms or some components in the culture or culture supernatant, it can be removed by the filter aid. The coagulant and/or filter aid to which vitamin K2 and *Bacillus natto* cells have been absorbed or aggregated can be collected as a filtration residue.

Food Product

If necessary, the filtrate is further subjected to subsequent treatment, such as micro filtration with a filter aid. Then the filtrate is concentrated using a concentrator, such as a reverse osmosis concentrator, to obtain a concentrate. Almost all the substances having a molecular weight of 100 or less can be removed by the reverse osmosis concentrator. Optionally, the concentrate may be subjected to sterile filtration through a membrane filter, for example, having a pore size of about 0.5 μm or about 0.2 μm. The concentration of vitamin K2 in the concentrate can be below 1 μg/g dry weight.

The concentrate is further concentrated into a paste. To the concentrate a food additive such as water-soluble dietary fibers, lactose, cellulose or the like is added in an appropriate amount, and the mixture is freeze-dried to form a powder or granule. The concentrate, paste, power or granule can be encapsulated. The concentrate, paste, power or granule can be used for producing a tablet. The tablet can be various types of surface-coated tablets, including a sugar-coated pill, depending on their use. Thus, the food product of the present invention can be produced.

The food product contains nattokinase, but can contain vitamin K2 only in an amount of below about 1 μg/g dry weight. The amount of vitamin K2 in the food product can be below the detection limit (about 0.001 μg/g dry weight). The content of nattokinase is without limitation, and preferably about 20 FU or more, more preferably about 1000 FU or more, and even more preferably about 2500 FU or more, per 1 g. The content of nattokinase can vary with the form of the food product. In the case of dry powder, the content can be about 5000 FU or more per 1 g, and can be about 10000 FU or more per 1 g. The activity of nattokinase can be detected, for example, by detecting any plaque formed on a fibrin plate according to the method as described in Experientia Vol. 43, pp. 11190-1111 (1987). In the present invention, nattokinase refers to an enzyme that is produced by *Bacillus natto* and has an ability of forming a clear plaque on a fibrin plate.

The activity of nattokinase and the amount of vitamin K2 can be determined in the following manner.

A: Measurement of Nattokinase Activity

Nattokinase is allowed to act upon fibrin, and the amount of acid-soluble low molecular degradation product is increased with degradation of fibrin. The increase in the degradation product is determined by measuring the absorbance of an ultraviolet ray (275 nm).

a-1: Preparation of an Aqueous Fibrinogen Solution

Seventy-two mg of fibrinogen (produced by Sigma Corp., fibrinogen fraction I derived from bovine blood plasma, Type I-S) is dissolved in 10 ml of 50 mM borax buffer (pH 8.5; containing 150 mM NaCl) to prepare a 0.72% (w/v) aqueous fibrinogen solution.

a-2: Preparation of a Thrombin solution

Thrombin (produced by Sigma Corp., derived from bovine blood plasma) is dissolved in 50 mM borax buffer so as to have a concentration of 1000/ml. When this solution is to be used, it is diluted 50 times (i.e., into 20 U/ml) with the borax buffer.

a-3: Activity Measurement

First, 1.4 ml of 50 mM borax buffer and 0.4 ml of aqueous fibrinogen solution are placed into a test tube, and then warmed at 37° C.±0.3° C. in a water bath for five minutes. Then, 0.1 ml of the thrombin solution is added thereto, and the mixture is stirred. This mixture is allowed to stand in the water bath for 10 minutes. Then, 0.1 ml of a sample solution is added to the mixture, and the mixture is stirred for 5 seconds, and then allowed to stand in the water bath. The mixture is stirred for 5 seconds at 20 minutes and 40 minutes after adding the sample solution. Sixty minutes after adding the sample solution, 2 ml of 0.2 M trichloroacetate solution is added thereto, and the mixture is stirred, and allowed to stand for an additional 20 minute period. The reaction mixture is centrifuged for 5 minutes at 15,000×g, and the absorbance (Ar) of the supernatant at 275 nm is measured.

As a control, 1.4 ml of 50 mM borax buffer and 0.4 ml of aqueous fibrinogen solution are placed into a test tube, and then warmed at 37° C.±0.3° C. in a water bath for five minutes. Then, 0.1 ml of the thrombin solution is added, and the mixture is stirred. This mixture is allowed to stand in the water bath for 10 minutes. Then, 2 ml of 0.2 M trichloroacetate solution is added thereto, and the mixture is stirred. Next, 0.1 ml of the sample solution is added to the mixture and stirred, and allowed to stand for 20 minutes. The reaction mixture is centrifuged for 5 minutes at 15,000×g, and the absorbance (Ac) of the supernatant at 275 nm is measured.

Nattokinase activity is determined according to the formula below:

$$A(FU/ml) = \{(Ar-Ac)/(0.01 \times 60 \times 0.1)\} \times D,$$

where D is the dilution ratio.

B. Quantification of Vitamin K2

As described below, a sample is prepared for HPLC measurement and vitamin K2 is measured by HPLC.

b-1: Preparation of a Sample for HPLC Measurement

First, 0.5 ml of a sample to be measured, 0.5 ml of water, and 1.5 ml of isopropanol are mixed and stirred, and then 5 ml of hexane is added thereto, and is stirred. The mixture is centrifuged at 1700×g for 10 minutes at 20° C. to give 4 ml of the supernatant (organic layer). The supernatant is concentrated, dried, and then dissolved in 100 µl of ethanol to give the solution of the sample.

B-2: HPLC Conditions

The HPLC conditions are as follows:

Column: Shimadzu STR ODS-2 4.6×250 mm
Eluant: 97% ethanol
Flow rate: 0.7 ml/min.
Detection: UV 254 nm Under these conditions, the retention time of vitamin K2 is between 16 and 17 minutes.

Production of Vitamin K2

According to the invention, *Bacillus natto* is cultured in a liquid medium to allow it to produce vitamin K2. Therefore, a *Bacillus natto* culture or culture supernatant thereof contains vitamin K2. The cultivation of *Bacillus natto* is as described above. The culture or culture supernatant is treated with at least one coagulant selected from the group consisting of an inorganic coagulant and a cationic polymer coagulant, with the proviso that the coagulant excludes chitosan, to separate vitamin K2. Since vitamin K2 can be absorbed or aggregated to the coagulant, vitamin K2 can be separated and collected by the subsequent recovery of the coagulant from the treated culture or culture supernatant. A filter aid can also be used to help the subsequent recovery of the coagulant. Therefore, preferably, the treated culture or culture supernatant is filtered to obtain a filtration residue that includes the coagulant and vitamin K2. From the filtration residue, vitamin K2 is extracted with an organic solvent. Alternatively, the treated culture or culture supernatant is centrifuged to obtain a precipitate including the coagulant and vitamin K2, and from the precipitate vitamin K2 is extracted with an organic solvent.

The extraction can be performed by adding an organic solvent to the filtration residue or the precipitate. Examples of the organic solvent include lower alcohols (such as methyl alcohol, ethyl alcohol, butyl alcohol, propyl alcohol and isopropyl alcohol), hexane, ethyl ether, acetone, chloroform, ethyl acetate and any combinations thereof. As the organic solvent, hexane-isopropyl alcohol (at the ratio of 3:2 by weight) is preferably used. Then, the extract is collected and the solvent is removed so as to obtain an oily product that contains vitamin K2. Further, vitamin K2 can be purified from this oily product, using any methods commonly used by those skilled in the art such as molecular distillation and steam distillation. Both the oily product that contains vitamin K2 and purified vitamin K2 can be formulated into the form such as oil, powder, granule, or tablet. The oily product that contains vitamin K2 or purified vitamin K2 can be applied in the food or pharmaceutical industry, and for medical treatments such as prevention of osteoporosis.

EXAMPLES

The following examples are provided to explain the present invention. It should be appreciated that the present invention is not limited thereby.

Example 1

A culture medium at pH 7 containing 1 wt % of polypeptone, 1 wt % of glucose, 0.5 wt % meat extract, and 0.2 wt % of NaCl was placed in a round bottom flask, inoculated with *Bacillus natto* isolated from natto thereto, and then incubated at 37° C. for 18 hours. The *Bacillus natto* culture thus obtained was inoculated into a seed culture tank containing the culture medium having the same composition as the culture medium in the round bottom flask, and incubated for 22 hours to give a *Bacillus natto* seed culture.

Then, a culture medium at pH 7.3 containing 6.25 wt % of corn starch, 3.09 wt % of defatted soybeans, 0.15 wt % of food additive grade calcium carbonate, 1.5 wt % of soybean oil, and 0.008 wt % of silicone was prepared. To the culture medium at pH 7.3, the *Bacillus natto* seed culture was added, and then incubated at 37° C. for 70 hours with aeration of 0.5 VVM. The resultant *Bacillus natto* culture contained 480 FU/ml of nattokinase and 5.7 µg of vitamin K2 per gram of culture.

Then, 4.4 g of disodium hydrogenphosphate was added to 100 g of the resultant *Bacillus natto* culture, and the mixture was stirred extensively, and then 3.3 g of a 35 wt % calcium chloride aqueous solution and 2.7 g of pearlite were added thereto and the mixture was stirred at room temperature for 30 minutes. The pH of the culture was adjusted to 7.2, and the culture was filtrated under reduced pressure to give a filtrate.

The activity of nattokinase and the amount of vitamin K2 in the filtrate were determined according to the procedures A and B described above, respectively. The results are shown in Table 1.

Example 2

First, 4.5 g of a 10 wt % of poly aluminum chloride aqueous solution and 1.8 g of pearlite were added to 100 g of the resultant *Bacillus natto* culture in Example 1, and the mixture was stirred at room temperature for 10 minutes. The pH of the culture was adjusted to 5.0, and the culture was filtrated under reduced pressure to give a filtrate. The activity of nattokinase and the amount of vitamin K2 in the filtrate were determined as in Example 1. The results are shown in Table 1. The poly aluminum chloride was obtained from TAKI CHEMICAL CO., LTD.

Example 3

The pH of 100 g of the resultant *Bacillus natto* culture in Example 1 was adjusted to 4.5, and 0.04 g of sodium polyacrylate (trade name: "AQUALIC FH" manufactured by NIPPON SHOKUBAI), 0.02 g of cationic polysaccharides (trade name: "Kiprogum NGK" manufactured by NIPPON STARCH CHEMICAL CO., LTD.) and 2.5 g of pearlite were added thereto, and the mixture was stirred at room temperature for 10 minutes and subjected to filtration under reduced pressure to give a filtrate. The activity of nattokinase and the amount of vitamin K2 in the filtrate were determined as in Example 1. The results are shown in Table 1.

Example 4

First, 10 g of an aqueous solution containing 0.2 wt % of a 30% hexamethylenediamine/epichlorohydrin polycondensate aqueous solution (trade name: "SANPOLY K-601" manufactured by SANKYO CHEMICAL INDUSTRIES, LTD.), and 2.5 g of pearlite were added to 100 g of the resultant *Bacillus natto* culture in Example 1, and the mixture was stirred at room temperature for 10 minutes. The pH of the culture was adjusted to 7.0, and the culture was filtrated under reduced pressure to give a filtrate. The activity of nattokinase and the amount of vitamin K2 in the filtrate were determined as in Example 1. The results are shown in Table 1.

Example 5

First, 10 g of an aqueous solution containing 0.2 wt % of a 50% dimethylamine/epichlorohydrin polycondensate aqueous solution (trade name: "SANPOLY K-108" manufactured by SANKYO CHEMICAL INDUSTRIES, LTD.), and 2.5 g of pearlite were added to 100 g of the resultant *Bacillus natto* culture in Example 1, and the mixture was stirred at room temperature for 10 minutes. The pH of the culture was adjusted to 7.0, and the culture was filtrated under reduced pressure to give a filtrate. The activity of nattokinase and the amount of vitamin K2 in the filtrate were determined as in Example 1. The results are shown in Table 1.

Comparative Example 1

Chitosan (manufactu8red by KYOWA TECNOS CO., LTD.) was dissolved in 0.18 wt % of acetic acid so that a 0.4% chitosan solution could be prepared. Then, 7.5g of the 0.4 chitosan solution was added to 100 g of the resultant *Bacillus natto* culture in Example 1, and 2.5 g of pearlite was added thereto, and the mixture was stirred at room temperature for 10 minutes. The mixture was filtrated under reduced pressure to give a filtrate. The activity of nattokinase and the amount of vitamin K2 in the filtrate were determined as in Example 1. The results are shown in Table 1.

TABLE 1

|  |  | Vitamin K2 *1 | | | Nattokinase *2 | | |
| --- | --- | --- | --- | --- | --- | --- | --- |
| No. | Treatment | Before filtration | After filtration | Removal (%) | Before filtration | After filtration | Retention (%) |
| Ex. 1 | Disodium hydrogenphosphate calcium chloride | 5.7 | below detection limit | 100 | 480 | 475 | 99 |
| Ex. 2 | Poly aluminum chloride | 5.7 | below detection limit | 100 | 480 | 478 | 99 |
| Ex. 3 | Sodium polyacrylate cationic coagulant of plant polysaccharides | 5.7 | 0.1 | 98 | 480 | 464 | 97 |
| Ex. 4 | Hexamethylenediamine/ epichlorohydrin polycondensate | 5.7 | below detection limit | 100 | 480 | 470 | 98 |
| Ex. 5 | Dimethylamine/ epichlorohydrin polycondensate | 5.7 | below detection limit | 100 | 480 | 470 | 98 |
| Comp. Ex. 1 | Chitosan | 5.7 | below detection limit | 100 | 480 | 475 | 00 |

*1 μ/g culture
*2 FU/ml culture

As evident from Table 1, almost all vitamin K2 was removed, while nattokinase was retained in the *Bacillus natto* culture, with any treatments in Examples 1 to 5, as in the case of conventionally known chitosan.

According to the method of the present invention-, vitamin--K2 can be removed from a *Bacillus natto* culture in a lower cost and a simpler manner than using chitosan. The thrombolytic activity of nattokinase would function more effectively by reducing the amount of vitamin K2 that should act on the blood coagulation system. Therefore, the method of the present invention is useful in producing a health food having an excellent efficacy.

Since the food product of the present invention contains little vitamin K2, it is possible to prevent the overintake of vitamin K2 and the thrombogenesis in healthy people. For the patients who are restricted to intake of vitamin K2, the food product of the present invention can be safely ingested to intake nattokinase.

Example 6

A *Bacillus natto* culture was prepared in the same manner as Example 1. To 20 kg of the *Bacillus natto* culture, 880 g of disodium hydrogen phosphate was added and mixed. The mixture was stirred extensively, and then 660 g of a 35 wt % calcium chloride aqueous solution was added and mixed. Then, 540 g of pearlite were added thereto and mixed. The resultant mixture was stirred at room temperature for 30 minutes. The pH of the mixture was adjusted to 7.2, and the mixture was filtrated under reduced pressure to give a filtration residue. The amount of vitamin K2 in the filtration residue was determined according to the procedure B described above, and found to be 308.8 µg wet weight of the filtration residue.

To 1 kg of the filtration residue, 5 kg of n-hexane was added and stirred at 40° C. for 24 hours in order to extract vitamin K2. The n-hexane fraction ($1^{st}$ n-hexane extract) was collected by filtration. To the filtrate residue, 4 kg of n-hexane was further added and stirred at 40° C. for 3 hours, and the n-hexane fraction ($2^{nd}$ n-hexane extract) was collected. The $1^{st}$ and $2^{nd}$ n-hexane extracts were collected, evaporated to remove the n-hexane, and distilled at 50° C., 100 HPa to obtain a crude oil. The resultant oil fraction was heated at 150° C. for 2 hours for deodorization. Thus, 95 g of an oily product that contains vitamin K2 at 2766 µg/g was obtained. To the thus-obtained oily product that contains vitamin K2, the following components were added to make the composition stated below, and mixed, and the mixture was then freeze-dried to obtain a powdered product:

| | |
|---|---|
| Oily product that contains vitamin K2 | 80.84 g |
| Gum arabic | 7.19 g |
| Sodium arginate | 6.45 g |
| Citric acid | 0.81 g |
| Sodium bicarbonate | 0.81 g |
| Ascorbyl palmitate | 0.40 g |

| -continued | |
|---|---|
| Calcium chloride | 0.29 g |
| Tocopherol | 0.04 g |

According to the method of the present invention, vitamin K2 can be collected from a *Bacillus natto* culture at a lower cost and a simpler manner than using chitosan.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

The invention claimed is:

1. A method for producing vitamin K2, comprising:
   culturing *Bacillus natto* in a liquid medium to obtain a *Bacillus natto* culture or culture supernatant thereof, wherein the culture or culture supernatant contains vitamin K2;
   treating the *Bacillus natto* culture or culture supernatant with an inorganic coagulant in combination with a phosphorus-containing coagulant, wherein the inorganic coagulant is calcium chloride and the phosphorus-containing coagulant is at least one selected from the group consisting of disodium hydrogenphosphate, sodium dihydrogenphosphate, potassium dihydrogenphosphate and tripotassium phosphate, so as to form a coagulant to which vitamin K2 from the *Bacillus natto* culture or culture supernatant is absorbed or aggregated;
   separating the coagulant to which vitamin K2 is absorbed or aggregated from the treated culture or culture supernatant;
   treating the coagulant to which vitamin K2 is absorbed or aggregated with an organic solvent for extraction;
   collecting an organic solvent extract;
   removing the organic solvent from the organic solvent extract; and
   obtaining an oily product that contains vitamin K2 from the extract from which the organic solvent has been removed.

2. The method of claim 1, wherein the separation is performed by filtration so as to obtain the coagulant to which vitamin K2 is absorbed or aggregated as a filtration residue.

* * * * *

UNITED STATES PATENT AND TRADEMARK OFFICE
CERTIFICATE OF CORRECTION

PATENT NO.        : 8,114,642 B2
APPLICATION NO.   : 11/823769
DATED             : February 14, 2012
INVENTOR(S)       : Shinsaku Takaoka et al.

It is certified that error appears in the above-identified patent and that said Letters Patent is hereby corrected as shown below:

Cover of the Patent, item (56), Column 2, OTHER PUBLICATIONS, Line 10, delete "Swilzerland" and insert -- Switzerland --

Signed and Sealed this
Twenty-fifth Day of September, 2012

David J. Kappos
*Director of the United States Patent and Trademark Office*